United States Patent [19]
Love et al.

[11] Patent Number: 6,077,217
[45] Date of Patent: Jun. 20, 2000

[54] SYSTEM AND METHOD FOR ASSEMBLING GRAFT STRUCTURES

[75] Inventors: Charles S. Love, Santa Barbara; Terrance J. Dahl, Solvang, both of Calif.

[73] Assignee: Ramus Medical Technologies, Inc., Santa Barbara, Calif.

[21] Appl. No.: 08/881,063

[22] Filed: Jun. 25, 1997

[51] Int. Cl.$^7$ .................................. A61F 2/06; B21F 3/04
[52] U.S. Cl. .......................... 600/36; 623/1.13; 242/447.3
[58] Field of Search .................................. 623/1, 12, 901, 623/1.13, 1.14; 600/36; 242/443, 447, 447.2, 447.3

[56] References Cited

U.S. PATENT DOCUMENTS

| | | |
|---|---|---|
| 3,408,659 | 11/1968 | Thiele et al. . |
| 3,562,820 | 2/1971 | Braun . |
| 3,894,530 | 7/1975 | Dardik et al. . |
| 3,974,526 | 8/1976 | Dardik et al. . |
| 3,988,782 | 11/1976 | Dardik et al. . |
| 4,300,244 | 11/1981 | Bokros . |
| 4,502,159 | 3/1985 | Woodroof et al. . |
| 4,539,716 | 9/1985 | Bell . |
| 4,728,328 | 3/1988 | Hughes et al. . |
| 4,731,073 | 3/1988 | Robinson . |
| 4,798,606 | 1/1989 | Pinchuk . |
| 4,801,299 | 1/1989 | Brendel et al. . |
| 4,820,298 | 4/1989 | Leveen et al. . |
| 4,822,361 | 4/1989 | Okita et al. . |
| 4,842,575 | 6/1989 | Hoffman, Jr. et al. . |
| 5,163,955 | 11/1992 | Love et al. . |
| 5,215,541 | 6/1993 | Nashef et al. . |
| 5,297,564 | 3/1994 | Love . |
| 5,326,370 | 7/1994 | Love et al. . |
| 5,326,371 | 7/1994 | Love et al. . |
| 5,372,821 | 12/1994 | Badylak et al. . |
| 5,423,885 | 6/1995 | Williams . |
| 5,423,887 | 6/1995 | Love et al. . |
| 5,425,741 | 6/1995 | Lemp et al. . |
| 5,489,298 | 2/1996 | Love et al. .................................. 623/2 |
| 5,545,208 | 8/1996 | Wolff et al. .................................. 623/1 |
| 5,556,414 | 9/1996 | Turi . |

FOREIGN PATENT DOCUMENTS

| | | |
|---|---|---|
| 8903621 | 1/1991 | Brazil . |
| 9003762 | 2/1992 | Brazil . |
| 760312 | 6/1967 | Canada .................................. 242/26 |
| 3714816 | 7/1995 | France . |
| 1217362 | 3/1986 | U.S.S.R. . |
| WO 94/22505 | 10/1994 | WIPO . |
| WO 95/25547 | 9/1995 | WIPO . |
| WO 97/09006 | 3/1997 | WIPO . |

OTHER PUBLICATIONS

Rendina, Erino A. et al. "Reconstruction of the Pulmonary Artery by a Conduit of Autologous Pericardium," *The Journal of Thoracic and Cardiovascular Surgery*, vol. 110, No. 3, pp. 867–868, 1995.

Hvass, U. et al. "Reconstruction des branches de l'artère pulmonarie avec des lambeaux pédiculès de péricarde autologue," *La Presse Mèdicale*, vol. 16, No. 9, pp. 441–443, Mar. 14, 1987.

Allen, Robert G. et al. "Modified Blalock Shunts Utilizing Pericardial Tube Grafts," *Journal of Pediatric Surgery*, vol. 12, No. 3, pp. 287–294, Jun. 1977.

Sako, M.D., Yoshio "Prevention of Dilatation in Autogenous Venous and Peridcardial Grafts in the Thoracic Aorta," *Surgery*, vol. 30, No. 1, pp. 148–160, 1951.

*Primary Examiner*—David H. Willse
*Attorney, Agent, or Firm*—Townsend and Townsend and Crew LLP

[57] ABSTRACT

A system and apparatus are disclosed for preparing tubular prostheses from a sheet of tissue and inner and outer helical frame components. The tissue is wrapped around the inner frame component over an assembly mandrel. The outer helical frame component is then transferred from an elongate support over a lead screw, onto the assembly mandrel by rotating the assembly mandrel and lead screw in a manner which positions the outer helical frame component in an appropriate manner. Optionally, the mandrel is collapsed to facilitate removal of the completed tubular prosthesis.

34 Claims, 7 Drawing Sheets

SYSTEM AND METHOD FOR ASSEMBLING GRAFT STRUCTURES

BACKGROUND OF THE INVENTION

1. Field of the Invention

The present invention relates generally to medical methods and devices, and more particularly to a method and apparatus for forming vascular prostheses from host tissue sources.

Coronary and peripheral atherosclerosis are characterized by partial or total occlusion of the arteries resulting from the accumulation of lipids, smooth muscle cells, connective tissue, and glycosaminoglycans on the arterial wall. Atherosclerosis of the coronary arteries is a particular problem and can cause angina and myocardial infarction (heart attack). Although many coronary lesions can be treated with percutaneous techniques, such as angioplasty and atherectomy, more tortuous and severely diseased arteries frequently require surgical intervention and bypass, commonly referred to as coronary artery bypass graft (CABG) surgery.

CABG surgery relies on the surgical attachment of a vascular graft to bypass the arterial occlusion in order to restore blood flow to the coronary vasculature. The nature of the vascular graft can have a significant impact on the ultimate success of the procedure. A preferred vascular graft is formed from autologous internal mammary artery (IMA), where the resulting grafts have a patency rate approaching 95% ten years following the procedure. The use of IMA grafts, however, is limited by their length, and the need to harvest the artery from the patient can result in post-surgical complications. The autologous saphenous vein is a second common source for vascular grafts. While generally available in the necessary lengths, the saphenous vein is not ideally suited for replacement as an arterial vessel, and patency rates at ten years are often below 50%. Moreover, removal of the saphenous vein from the leg can also cause post-surgical complications.

Because of the limitations on autologous vascular sources, a variety of synthetic and non-autologous biological prostheses have been proposed. Common synthetic prostheses are formed from Dacron® and PTFE, and can perform well when employed in larger diameters, i.e., above 6 mm. Smaller synthetic prostheses, however, occlude at a relatively high rate. Non-autologous biological conduits which have been utilized as vascular prostheses include human umbilical vein grafts and bovine internal mammary arteries. Synthetic grafts have also been seeded with human and other mammalian cells or proteins, e.g., collagens, in an effort to improve their long-term patency rate. Presently, however, none of these approaches has demonstrated long-term patency, particularly in smaller diameter grafts.

Of particular interest to the present invention, preparation of vascular prostheses from autologous pericardium has been proposed. Pericardial tissue is harvested from the patient and formed into a tubular graft by suturing along a longitudinal line. While promising, the use of sutures can result in an irregular seam which, in turn, can cause turbulent blood flow and result in clot formation. Moreover, such grafts are unsupported and subject to kinking and collapse. The grafts further lack an inherently round geometry and are subject to dimensional changes, e.g., elongation and aneurysmal formation. Because of the dimensional uncertainty, it is difficult to match such grafts to the precise dimensional requirements of the particular application, e.g, caliber and length. The suturing of vascular prostheses from pericardium is labor intensive and time consuming, and the resulting structures are subject to rupture and other structural failure. Thus, the outcome of using sutured pericardial tissue grafts is uncertain at best.

A significant improvement over such prior autologous pericardial graft structures is disclosed in copending application Ser. No. 08/580,582, filed on Dec. 29, 1995, and assigned to the assignee of the present application, the full disclosure of which is incorporated herein by reference. In that copending application, a prosthetic graft is formed by wrapping a sheet of tissue over a first helical frame which is optionally supported on a mandrel. A second helical frame is then placed over the tissue-wrapped mandrel to complete the graft structure. No suturing is necessary, and the resulting structure is dimensionally stable, available in a variety of lengths, and biologically compatible.

Despite such advantages, the graft structures described in the copending application can be cumbersome to fabricate, particularly when the fabrication is carried out in the operating room after harvesting of the tissue and before performance of a CABG or other grafting procedure. For example, placement of the outer helical frame over the tissue-wrapped inner frame can be difficult, particularly when trying to properly align adjacent turns of the outer helical frame between corresponding turns of the inner helical frame. Removal of the completed graft structure from the assembly mandrel can be difficult. Both the helical frames and the tissue are at risk of damage, and it is difficult to achieve repeatable, consistent graft structures.

For these reasons, it would be desirable to provide improved methods and apparatus for forming tubular prostheses from patient tissue over tubular support frames. It would be particularly desirable to provide methods and apparatus which permit the rapid placement of such helical outer frame components over an assembly mandrel with a high degree of accuracy and repeatability, and which further permit and facilitate removal of the fully formed prosthesis from the assembly mandrel without damage to either the tissue or the helical support structures. Such methods and systems should be suitable for preparing tubular prostheses having a wide range of diameters and lengths, and should be relatively easy to use while minimizing any chance of improper use. The present invention will address at least some of the objectives set forth above.

2. Description of the Background Art

U.S. Pat. No. 4,502,159, describes a vascular prosthesis made by suturing glutaraldehyde-treated pericardial tissue along a longitudinal seam. SU 1217362 (Abstract) describes reinforcing arteries by securing pericardial tissue over the artery. U.S. Pat. No. 3,562,820, describes forming tissue-containing prostheses over removable mandrels. The use of glutaraldehyde and other agents for treating tissue and prosthetic devices to reduce antigenicity is described in U.S. Pat. Nos. 3,988,782; 4,801,299; 5,215,541, and Brazilian applications 89/03621 and 90/03762. U.S. Pat. No. 4,539,716, describes the fabrication of an artificial blood vessel from collagen and other natural materials. U.S. Pat. Nos. 3,894,530 and 3,974,526, describe the formation of vascular prostheses from the arteries or veins present in the umbilical cord. U.S. Pat. No. 5,372,821, describes the use of tissue for forming artificial ligament grafts for use in orthopedic procedures. U.S. Pat. No. 3,408,659, describes the preparation of vascular artificial prostheses from other body lumens. French application FR 2,714,816, (Abstract) discloses a helically supported vascular prosthesis. A number of medical literature publications describe the use of vascular prostheses formed form tissue. See, for example, Rendina et al.

(1995) *J. Thorac. Cardiovasc. Surg.* 110:867–868; Hvass et al. (1987) *La Presse Médicale* 16:441–443; Allen and Cole (1977) *J. Ped. Surg.* 12:287–294; and Sako (1951) *Surgery* 30:148–160. Other patents and published applications relating to synthetic vascular grafts include U.S. Pat. Nos. 4,728,328; 4,731,073; 4,798,606; 4,820,298; 4,822,361; and 4,842,575; and PCT publications WO 94/22505 and WO 95/25547. Patents and published applications relating to kits for preparing replacement heart valves from pericardial and other autologous tissue sources are described in U.S. Pat. Nos. 5,163,955; 5,297,564; 5,326,370; 5,326,371; 5,423,887; and 5,425,741.

SUMMARY OF THE INVENTION

The present invention provides improved methods, systems, and apparatus for forming tubular prostheses from animal tissue, usually autologous tissues from the patient who is to receive the prosthesis. The tubular prostheses are of the type which comprise an inner tubular frame, usually an inner helical member, a sheet of tissue wrapped around the inner tubular frame, and a second helical frame disposed over the wrapped tissue. The tissue is usually wrapped around the inner frame more than once, and the resulting tissue "sleeve" is captured between the inner and outer frames in the manner described in copending application Ser. No. 08/580,582, the full disclosure of which has previously been incorporated herein by reference.

The methods of the present invention are particularly suitable for performance in the operating room as part of a procedure for implanting the prosthesis. Thus, the methods herein will usually be performed at a point after the tissue has been harvested and prior to the implantation, and it is thus highly desirable that the methods be expeditious, relatively simple to carry out, and present minimum chance for error. The methods, systems, and apparatus of the present invention are very simple to use, reliably form the desired vascular prosthesis with proper alignment of the various components, and present minimum opportunity for error. In particular, the present invention provides for the simple and accurate placement of both an inner helical member and an outer helical member while facilitating wrapping of the tissue therebetween. The present invention further facilitates removal of the assembly mandrel so that the final prosthetic structure can be removed from the assembly mandrel with minimum risk of damage.

In a first aspect, the method of the present invention for forming a tubular prosthesis comprises providing a sheet of tissue, typically autologous tissue which is prepared by the procedures described below. The sheet of tissue is wrapped over a tubular inner frame member which, in turn, is disposed over a mandrel. A helical outer frame component is then placed over the wrapped tissue to form the tubular prosthesis. The mandrel is then collapsed and axially withdrawn from the tubular inner frame member to leave the tubular prosthesis ready for trimming prior to use.

In preferred embodiments of this method, the wrapping step may comprise placing an edge of the tissue over the tubular inner frame member, and thereafter rotating the mandrel to wrap at least one and one-half turns of the tissue thereover, usually from one and one-half to three turns. Preferably, two turns of the tissue will be wrapped in order to provide a prosthesis which does not need suturing to prevent leakage. Preferably, although not necessarily, the inner tubular member will comprise a helical frame member having a pitch which is the same as that of the outer helical frame member so that the inner and outer helical members are aligned in parallel over the length of the prosthesis.

Placement of the helical outer frame component over the wrapped tissue will preferably comprise rotating the mandrel to draw the helical outer frame component over the wrapped sheet of tissue, and preferably further comprise guiding the helical outer frame component as it is being drawn over the wrapped sheet of tissue. The guiding step will usually comprise rotating a lead screw, where the helical outer frame component is received in and advanced by a helical groove on the lead screw as it is rotated. The mandrel collapsing step will usually comprise withdrawing an inner support rod from an outer collapsible shell, e.g. at least two axial runners which are aligned over the cylindrical support rod.

In a second aspect, the method of the present invention for forming a tubular prosthesis comprises providing a sheet of tissue and wrapping the sheet of tissue over a tubular inner frame. The wrapped tubular inner frame is then axially aligned with a helical outer frame component, and an end of the helical outer frame component coupled to the wrapped tubular inner frame. By then rotating the tissue-wrapped inner frame, the helical outer frame is drawn over the outer surface of the tissue.

In preferred embodiments of this aspect, the method further comprises guiding the helical outer frame component as the tissue-wrapped inner frame is rotated so that successive turns of the component are laid over said tissue-wrapped inner frame at a substantially even pitch. The guiding step conveniently comprises rotating a lead screw which is axially aligned with the tissue-wrapped inner frame and the helical outer frame component, where the helical outer frame component is received in and advanced by a helical groove on the lead screw. Typically, the tubular inner frame is disposed over a mandrel, and the rotating step comprises rotating the mandrel. optionally, the mandrel may be radially collapsed in order to facilitate removal of the completed tubular prosthesis from the mandrel.

In a first aspect of the apparatus of the present invention, a tubular prosthesis assembly system comprises a base, an elongate lead screw rotatably mounted on the base, an elongate support for a helical outer frame component mounted on the base and parallel to the lead screw, and a prosthesis assembly mandrel removably mounted on the base and parallel to the lead screw and the elongate support. The prosthesis assembly mandrel and the elongate support member are disposed on opposite sides of the lead screw so that a helical outer frame component (which can be disposed over the elongate support but which does not form part of the tubular prosthesis assembly) can pass from the elongate support, over the lead screw, to the prosthesis assembly mandrel. The assembly further comprises a driver for synchronously rotating the lead screw and the prosthesis assembly mandrel in order to transfer the helical outer frame component from the elongate support to the prosthesis assembly mandrel. The lead screw and driver are configured to advance the axial position of the helical outer frame component over the exterior of the rotating prosthesis assembly mandrel so that the outer helical frame component will be precisely and accurately aligned in the desired pattern thereover, typically, at a pitch which matches that of an inner helical support member underlying tissue which is placed over the prosthesis assembly mandrel.

In preferred embodiments of the tubular prosthesis assembly system, the prosthesis assembly mandrel is radially collapsible. More preferably, the prosthesis assembly mandrel comprises a collapsible outer shell and an inner support rod, where removal of the inner support rod allows the outer shell to collapse to facilitate removal of a completed prosthesis therefrom.

In a second aspect of the apparatus of the present invention, a prosthesis assembly mandrel comprises an elongate cylindrical mandrel which is radially collapsible, a helical inner frame component is disposed over the elongate cylindrical mandrel. Typically, the elongate cylindrical mandrel comprises an inner support rod and an outer collapsible shell disposed thereover. Removal of the inner support rod axially from the outer shell permits the radial collapse of the shell. Typically, the prosthesis assembly mandrel has an outer diameter (when non-collapsed) in the range from 2 mm to 8 mm, and a length in the range from 15 cm to 50 cm.

DESCRIPTION OF THE SPECIFIC EMBODIMENTS

The present invention provides methods, systems, and apparatus for the preparation of vascular prostheses, also referred to as vascular grafts, intended for use in medical procedures requiring replacement or bypass of a patient's blood vessels. Most commonly, vascular prostheses will be used in peripheral vascular bypass, coronary artery bypass (CABG) procedures, but they also may find use in aneurysm repair; vascular access shunts; vessel reconstruction, such as pulmonary outflow tract and aortic outflow tract; as a conduit for valvular repair; and the like.

The tissue employed in the vascular prosthesis will be obtained from a human or other animal source, usually but not necessarily being obtained from the patient or host into which the prosthesis is to be implanted. The tissue may comprise any body tissue having sufficient strength and elasticity to act as the primary component of the prosthesis, usually being obtained from the pericardium or a fascial layer, such as the fascia lata. Other tissue sources include rectus sheath and venous tissues. The tissue will be harvested by conventional techniques, such as those described in Love, *Autologous Tissue Heart Valves*, R. G. Landes Co., Austin, Tex., 1993, Chapter 8.

The amount of tissue harvested will depend on the size of the vascular prosthesis to be prepared. Typically, the sheet of tissue initially obtained will be generally rectangular, having a length in the range from about 5 cm to 35 cm, usually 5 cm to 15 cm for pericardium, and a width in the range from about 2 cm to 20 cm, usually about 2 cm to 5 cm for pericardium. After harvesting, the tissue will be trimmed to size, usually using a cutting die, stencil, or other pattern-forming device capable of trimming the tissue to the dimensions required. The cut-tissue dimensions, of course, will depend on the dimensions of the vascular prosthesis to be formed. Typically, the sheet will be cut into a rectangular pattern having a length and width in the ranges set forth above. The length should be sufficient to provide the desired prosthesis length, and the width should be sufficient to wrap over the prosthesis diameter from one and one-half to three turns, usually about two times. The use of the fabrication method of the present invention lessens the need from precision in trimming the tissue.

After harvesting but usually before trimming, the tissue will be treated by conventional methods to enhance its stability and durability. For example, the tissue may be briefly immersed in a cross-linking solution, such as glutaraldehyde, in order to fix the tissue. It has been found that glutaraldehyde-treated tissue remains antigenically compatible with the host from which it has been harvested. Suitable techniques for treating the harvested tissue with glutaraldehyde are described in Love, supra., Chapter 5.

While it is preferred that the tissue be obtained from the patient in which the vascular prosthesis is to be implanted (referred to as "autologous" tissue), it is also possible to obtain tissue from other human and animal sources. For example, tissue could be obtained from human cadavers, including frozen (cryo-preserved) cadaver tissue, treated with the cross-linking or other preserving agent, and then employed to make vascular prostheses according to the teachings herein. Tissue could also be obtained from non-human animal sources, such as bovine tissue, porcine tissue, and the like. It would also be possible to use luminal tissues, such as venous tissues, e.g., human and non-human saphenous veins. While a particular advantage of the present invention is it allows the use of non-luminal tissues to form vascular and other graft structures, the use of the frames of the present invention would also be advantageous in supporting saphenous vein grafts along their lengths. The saphenous or other veins can either be split longitudinally, and formed as described hereinafter for other flat tissue sources, or alternatively could be placed intact over an inner stent with a second stent or sheath then being placed over the exterior of the vein.

Preferably, the grafts of the present invention will be formed from a single piece of tissue having a length which is generally equal to the length of the graft and having a single overlap extending longitudinally down the length of the graft. Other graft constructions, however, will be possible. For example, a single long, relatively narrow strip of tissue could be wrapped spirally around the graft, thus having a spiral overlap extending down the length of the graft. As a further alternative, two or more tissue sections could be wrapped around the frame to form the graft of the present invention in a variety of geometries. While the preferred tissue geometry will be illustrated and described hereinafter, it is appreciated that the present invention is not so limited.

In the exemplary embodiment, the tissue will be overlapped by the requisite amount and will be held together by the tubular support frame, as described in detail hereinafter. In some cases, however, it may be further desirable to provide adhesives, such as fibrin glues, biological adhesives, synthetic glues (cyanoacrylates), or the like, to bond the overlapping layers. It may also be possible to provide laser welding of the tissue layers together, also to enhance the bonding. It would also be possible to suture the layers together, although this will generally be less preferred for the reasons set forth above in the Background section. It would further be possible when employing an adhesive to join the adjacent tissue edges together in an abutting fashion, forming an axially extending butt-joint, although this method is not presently preferred.

The tubular prostheses will be formed between inner and outer tubular frame components which are typically composed of a non-biologic material having sufficient strength to maintain the rolled tissue in a tubular geometry with a substantially unrestricted lumen therethrough, but with sufficient flexibility to allow the prosthesis to be bent and with sufficient compliance to allow the prosthesis to accommodate pulsatile blood flow. Usually, the tubular frame components will be made from a spring metal, such as a spring stainless steel. A preferred material is alloy Nitinol SE508 (Nitinol Devices and Components, Inc., Fremont, Calif. 94539). The frame could also be formed from plastic materials having the requisite strength and flexibility requirements, such as thermoplastics. A third alternative would be thermoplastic-covered metal wires. The use of both plastics and thermoplastic-covered wires is advantageous if the frame is trimmed prior to use since the plastic materials will reduce the formation of sharp edges on the frame. Thermoplastic frame materials can also permit sewing or suturing through the frame. Both metal and plastic frame components may optionally be covered with polyester (Dacron®) in order to enhance biocompatibility and non-immunogenicity.

The dimensions of the tubular frame components will define the dimensions of the vascular prosthesis. Typically, the components will each have a diameter in the range from about 1 mm to 30 mm, usually from 3 mm to 25 mm, and a length in the range from 1 cm to 45 cm, usually from 1 cm to 25 cm, and may usually range from 5 cm to 15 cm. The rolled tissue supported between the frame components may extend slightly beyond the ends of the frame, typically by a distance in the range from 1 mm to 10 mm, usually from 2 mm to 6 mm. Such tissue extensions can facilitate suturing of the prosthesis to form end-to-end and end-to-side anastomoses in performing CABG and other procedures.

In all cases, the outer tubular frame member will be a helical outer frame component, e.g. a helical coil having the dimensions and composed of the materials described above. Usually, the inner helical frame member will be a substantially identical helical component, but not necessarily. The inner tubular frame member could be a mesh, a braid, a diamond-shaped lattice similar to a Palmaz-Schatz stent, or the like. The use of a pair of helical elements as the inner and outer frame members, however, is greatly preferred so that the outer helical frame components is disposed between the turns of the inner helical frame component, usually with an identical pitch and diameter, as described below.

Figure 1:
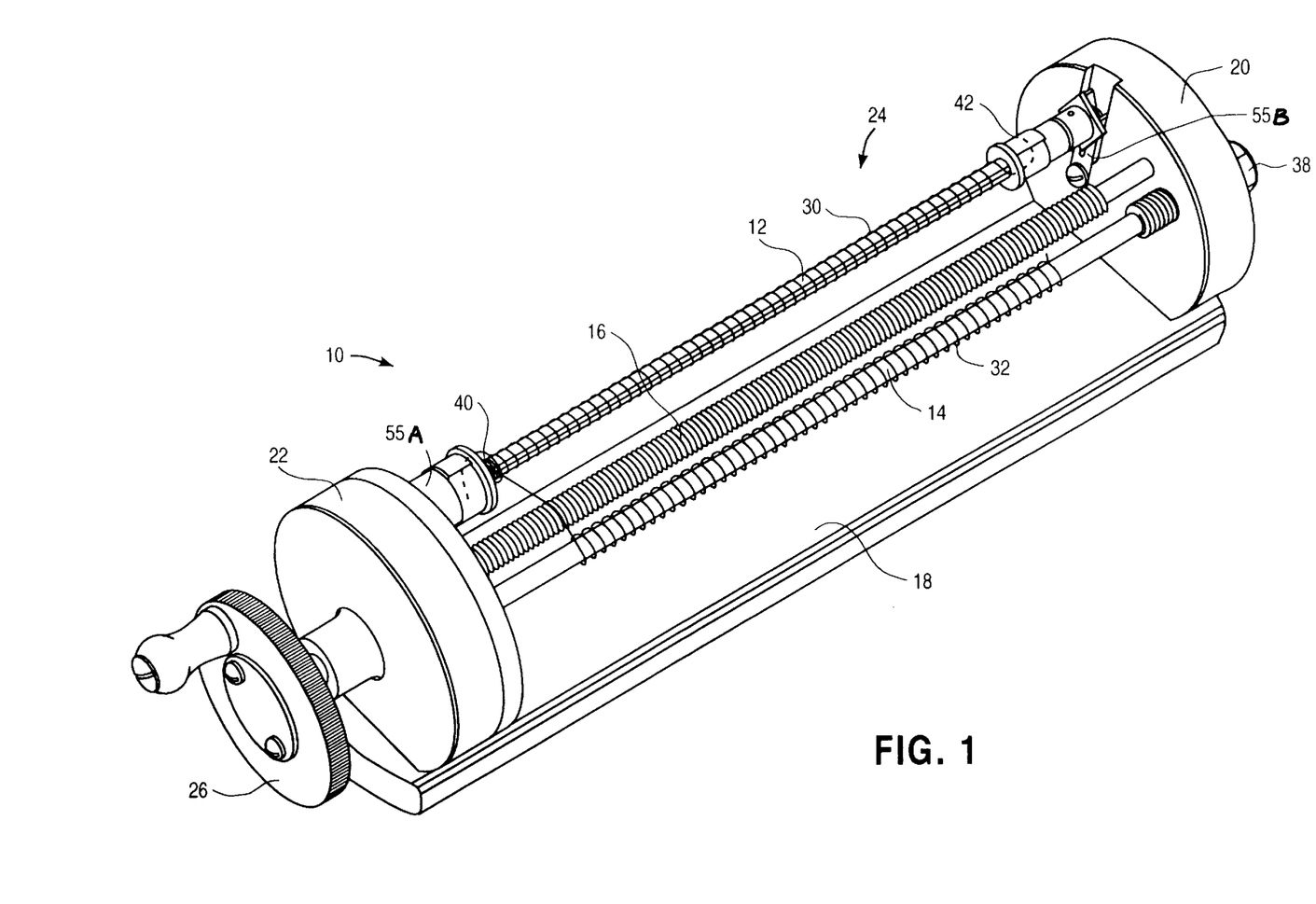
FIG. 1 is an isometric view of a tubular prosthesis assembly system constructed in accordance with the principles of the present invention.

Referring now to FIG. 1, a tubular prosthesis assembly system 10 according to the present invention comprises a prosthesis assembly mandrel 12, an elongate support 14, and a lead screw 16 mounted on a base structure 18. The base structure 18 comprises a first upright support 20 and a second upright support 22, which together define a working space of volume 24 therebetween which receives each of the mandrel 12, support 14, and lead screw 16. The prosthesis assembly mandrel 12 and lead screw 16 are both rotatable using a crank handle 26 which is coupled to the mandrel and lead screw through a drive assembly 28 (FIG. 4) which is located in the second upright support 22. The prosthesis assembly mandrel 12 is removable from the base structure 18 to facilitate placement of an inner helical frame component 30 thereover and removal of the completed tubular prosthesis therefrom. The lead screw 16, in contrast, need not be removable (other than with complete disassembly of the system 10, but could be if desired for any reason). The elongate support 14 will also preferably (but not necessarily) be removable to facilitate placement of an outer helical frame component 32 thereover prior to assembly of the prosthesis. By "removable" it is meant that both the prosthesis assembly mandrel 12 and the elongate support 14 may be conveniently mounted and de-mounted from the base structure 18 without having to significantly disassemble the base structure. In the case of the exemplary system 10, the mandrel 12 is mounted and removed by snapping radially in and out of the retainer 55 then sliding axially in and out of the drive coupling 55-b. In the case of elongate support 14, a set screw 38 can be loosened to permit removal. A variety of other, even more convenient, assembly and removal mechanisms could be provided.

The helical frame components 30 and 32 will usually have identical dimensions, i.e., diameter, length, and pitch. The diameter and length will be within the ranges set forth above, and the pitch, i.e., distance between successive turns of the helix, will usually be in the range from 0.5 mm to 5 mm, usually being from 1 mm to 3 mm, and preferably being from about 2 mm. It is desirable to increase the pitch as much as possible, while maintaining sufficient capture of the tissue therebetween to prevent fluid leakage from the prosthesis and ballooning (aneurysm) of the prosthesis. Thus, it will frequently be possible to increase the pitch of the helical support elements 14 and 16 by also increasing the amount of overlap of the tissue.

Figure 2:
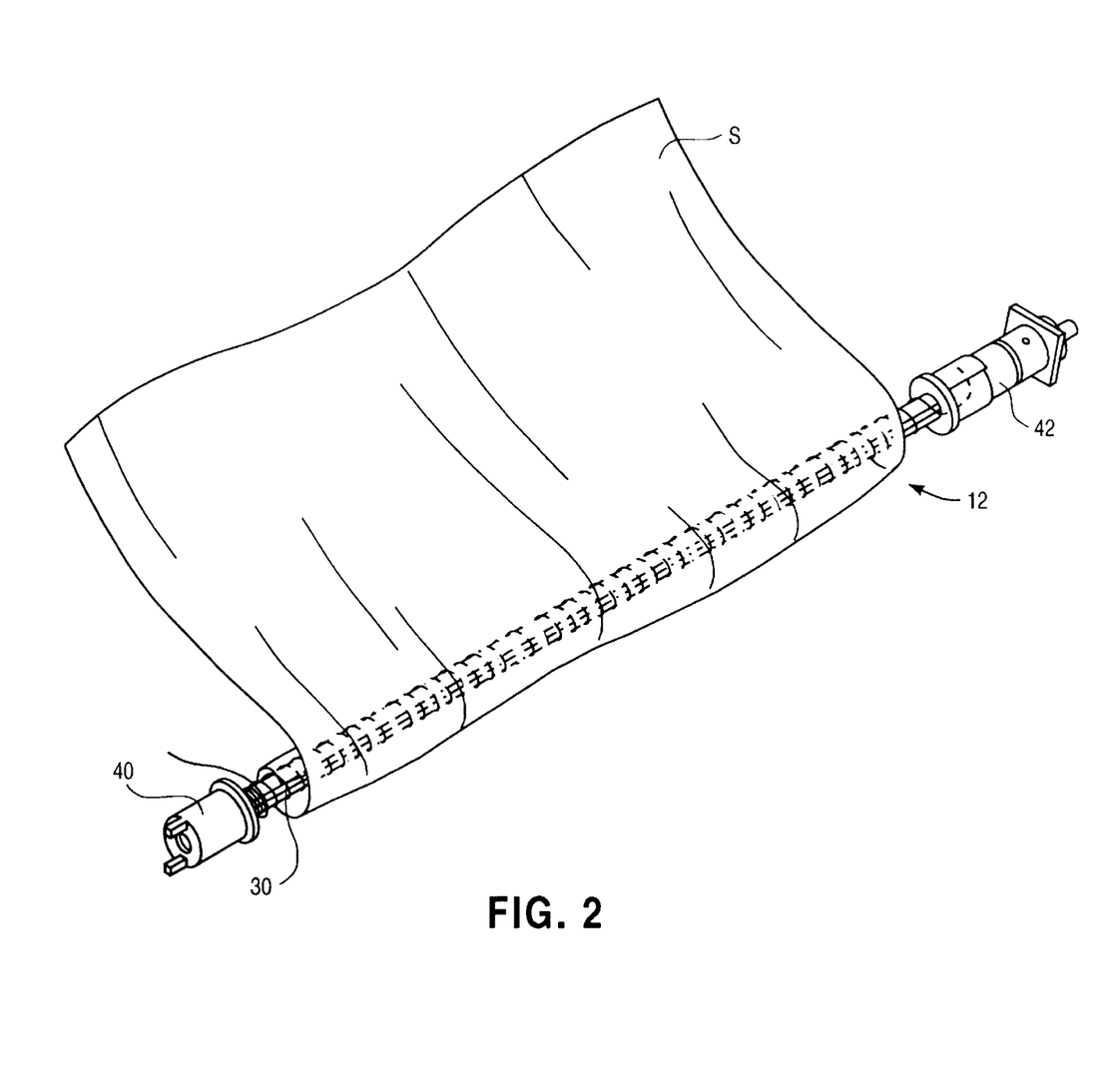
FIG. 2 illustrates the prosthesis assembly mandrel of the tubular prosthesis assembly system of FIG. 1 having a sheet of tissue wrapped thereover.

Referring now to FIG. 2, a tissue sheet S prepared as described above will be wrapped over the prosthesis assembly mandrel 12, as illustrated. Preferably, the tissue sheet S will be wrapped at least two full times over the mandrel 12, usually between two times and two and one-half times. The tissue will be wrapped over the inner helical frame component 30 which will usually be pre-placed on mandrel 12 prior to the start of the assembly procedure usually at a central manufacturing location. In such cases, the assembly mandrel 12 and inner helical frame component will be supplied together, optionally in a sterilized form. Alternatively, the combination could be sterilized at the hospital prior to use by conventional sterilization techniques, such as ethylene oxide sterilization.

The tissue sheet S is wrapped over the prosthesis assembly mandrel 12 between a drive collet 40 and non-drive collet 42. The collets 40 and 42 serve to hold the various components of the mandrel 12 together, as will be described in more detail in connection with FIG. 3. When mounted on the base structure 18, the collet 42 permits free rotation of the main portion of the assembly mandrel 12, while the collet 40 is directly driven by the drive assembly 28, as described later in connection with FIG. 4.

Figure 3:
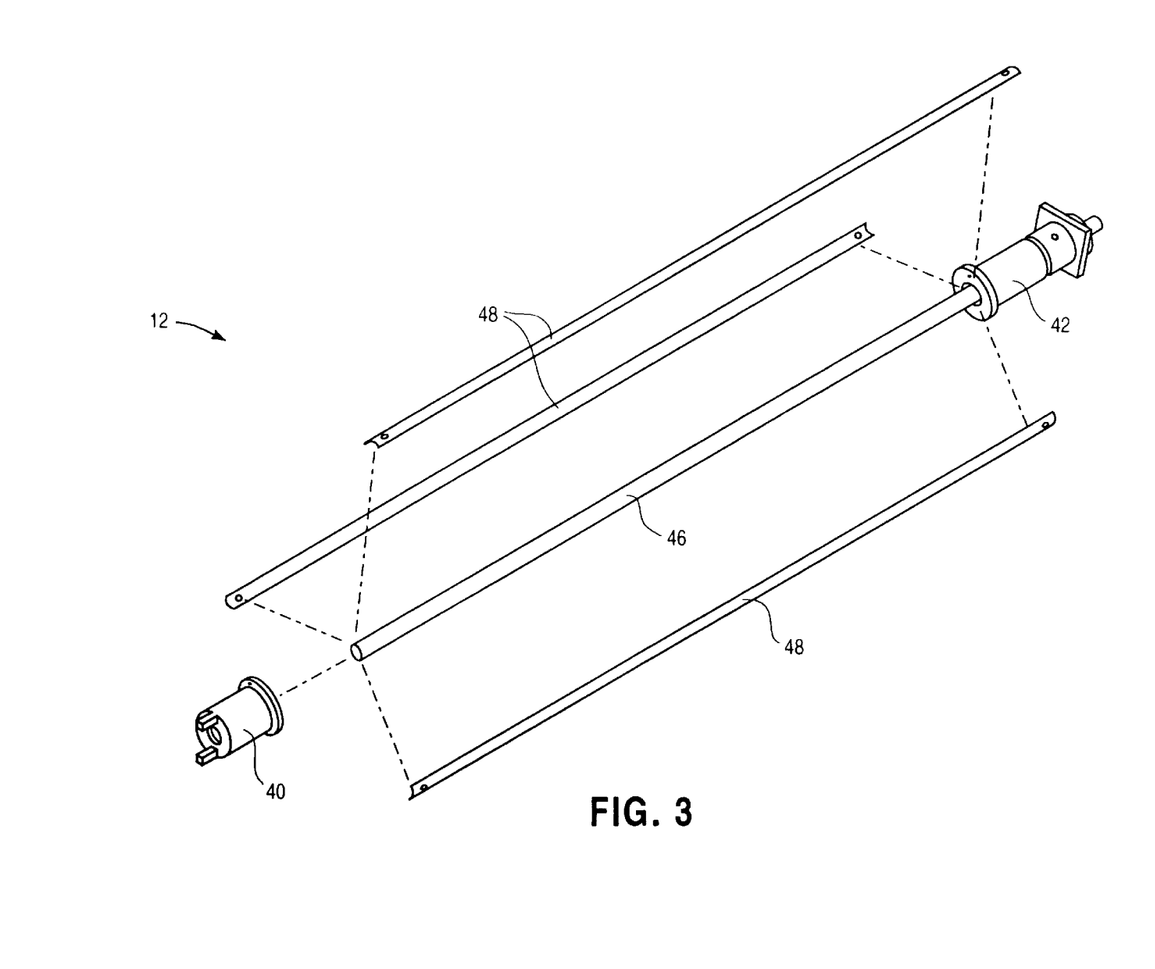
FIG. 3 is an exploded view of the prosthesis assembly mandrel of FIG. 2.

Referring now to FIG. 3, the prosthesis assembly mandrel 12 comprises a central core 46, which is typically polytetrafluoroethylene (PTFE) rod having a diameter in the range from 2 mm to 30 mm. Three axial ribs or runners 48 are closely received over the outer surface of the core 46 and are held in place by the collets 40 and 42. The inner helical frame component 30 is placed over the core 46 and runners 48 of the mandrel 12. The completed tubular prosthesis may be removed from the mandrel 12 by first axially withdrawing the core member to permit radial collapse of the runners 48 which together define a radially collapsible shell, and then removing both collets 40 and 42. It will be appreciated that a wide variety of other radially collapsible shells, such as a thin polymeric sheath, could also find use.

Figure 4:
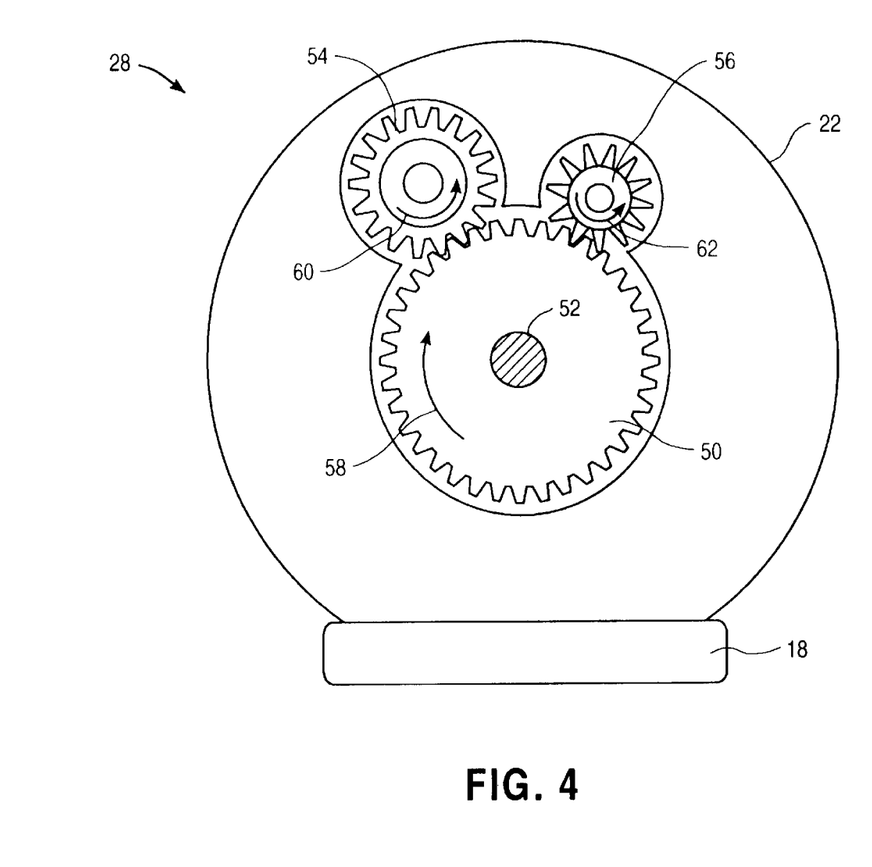
FIG. 4 is a side view of the drive mechanism of the tubular prosthesis assembly system of FIG. 1.

Referring now to FIG. 4, driver assembly 28 disposed in the second upright support 22 comprises a central gear 50 which is driven directly by the crank handle 26 through a connecting rod 52. The central gear 50, in turn, drives a first spur gear 54 and a second spur gear 56, where the first spur gear is connected to a socket 55 which receives the drive collet 40 of the prosthesis assembly mandrel 12 when said mandrel is mounted on the base structure 18. The second spur gear drives the lead screw 16. A ratchet or other rotational limit (not shown) will be provided so that the crank handle 26 can be rotated only in the clockwise direction indicated by arrow 58, which in turn drives the spur gears 54 and 56 in the counter-clockwise directions, as indicated by arrows 60 and 62.

Figure 5:
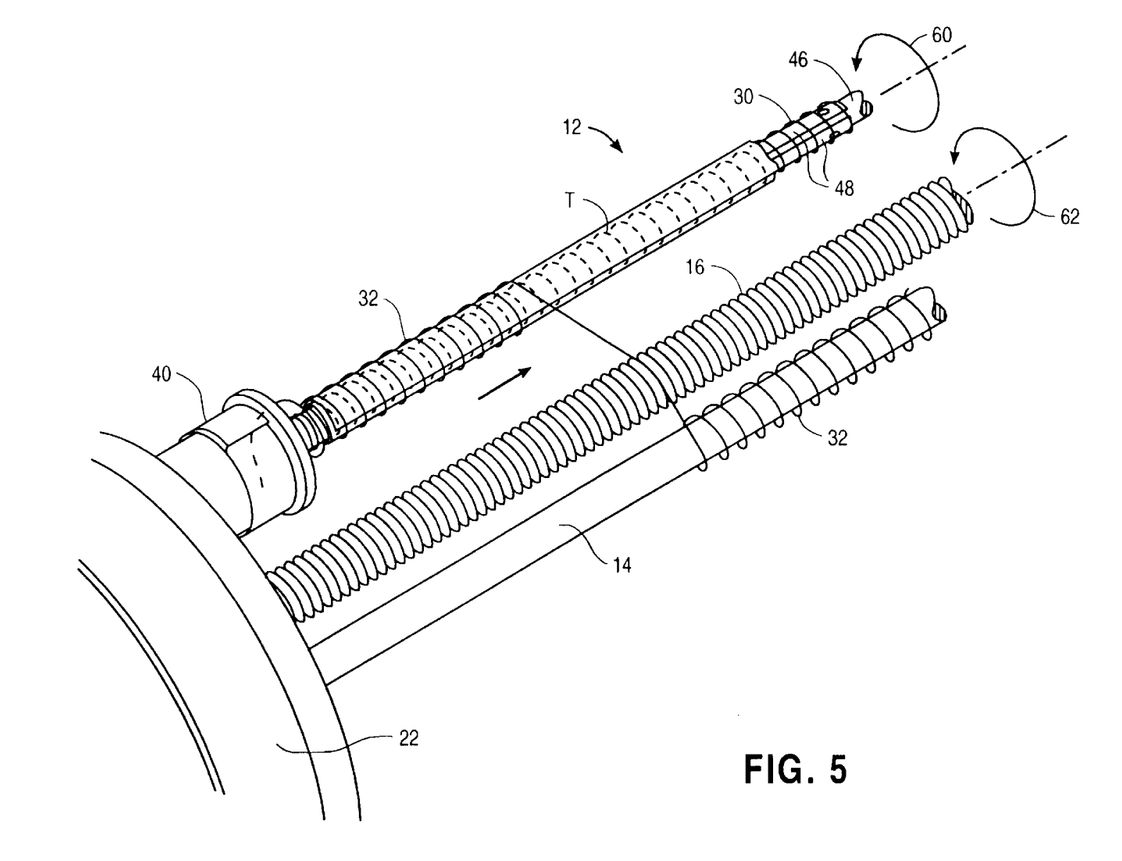
FIG. 5 is a detailed view of the prosthesis assembly mandrel, elongate support, and lead screw of the tubular prosthesis assembly system of FIG. 1, showing advancement of an outer helical frame component from the elongate support, over the lead screw, to the prosthesis assembly mandrel.

Referring now to FIG. 5, the tubular prosthesis assembly system 10 is particularly intended to transfer the outer helical frame component 32 from the elongate support 14 to the tissue-wrapped prosthesis assembly mandrel 12 so that the adjacent turns of the outer helical frame component 32 are aligned over the inner helical frame component 30 with an identical pitch, but spaced apart by 180°, i.e. the inner and outer helical coils will run parallel to each other but spaced apart by a length equal to one-half the pitch length. This is accomplished by first attaching a free end of the outer helical frame component 32 to the prosthesis assembly mandrel 12 near or on the drive collet 40, as shown in FIG. 1. The free end of the outer helical frame component 32 will be attached so that it is positioned between adjacent turns of the inner helical frame component 30. The portion of the outer helical frame component 32 between the prosthesis assembly mandrel 12 and the elongate support 14 will be positioned in a groove on the lead screw 16, where the groove will guide and advance the outer helical frame component 32 as the mandrel 12 and lead screw 16 are rotated using the crank handle 26. Once the free end of the outer helical frame component 32 has been attached, the remaining length of the component may be transferred simply by rotating crank handle 32 in the clockwise direction, which causes rotation of both the mandrel 12 and lead screw 16 in the counter-clockwise direction (as shown by arrows 60 and 62 in FIG. 5). The pitch of the grooves on lead screw 16 and relative rotational rates defined by gears 50, 54, and 56 of the drive assembly 28 are selected so that the turns of the outer helical frame component 32 are transferred and advanced at a pitch identical to that of the inner helical frame component 30. The natural pitch of the outer helical frame component, of course, will match that at which it is being transferred.

As illustrated in FIG. 5, the outer helical frame component 32 is mounted to freely rotate over the elongate support 14. Thus, there is no drag or friction applied to the outer helical frame component as it is being transferred, other than the natural spring coil force which resists the transfer. In some cases, however, it may be desirable to tension the outer helical frame components 32 as it is transferred by placing some friction on the component.

Figure 6:
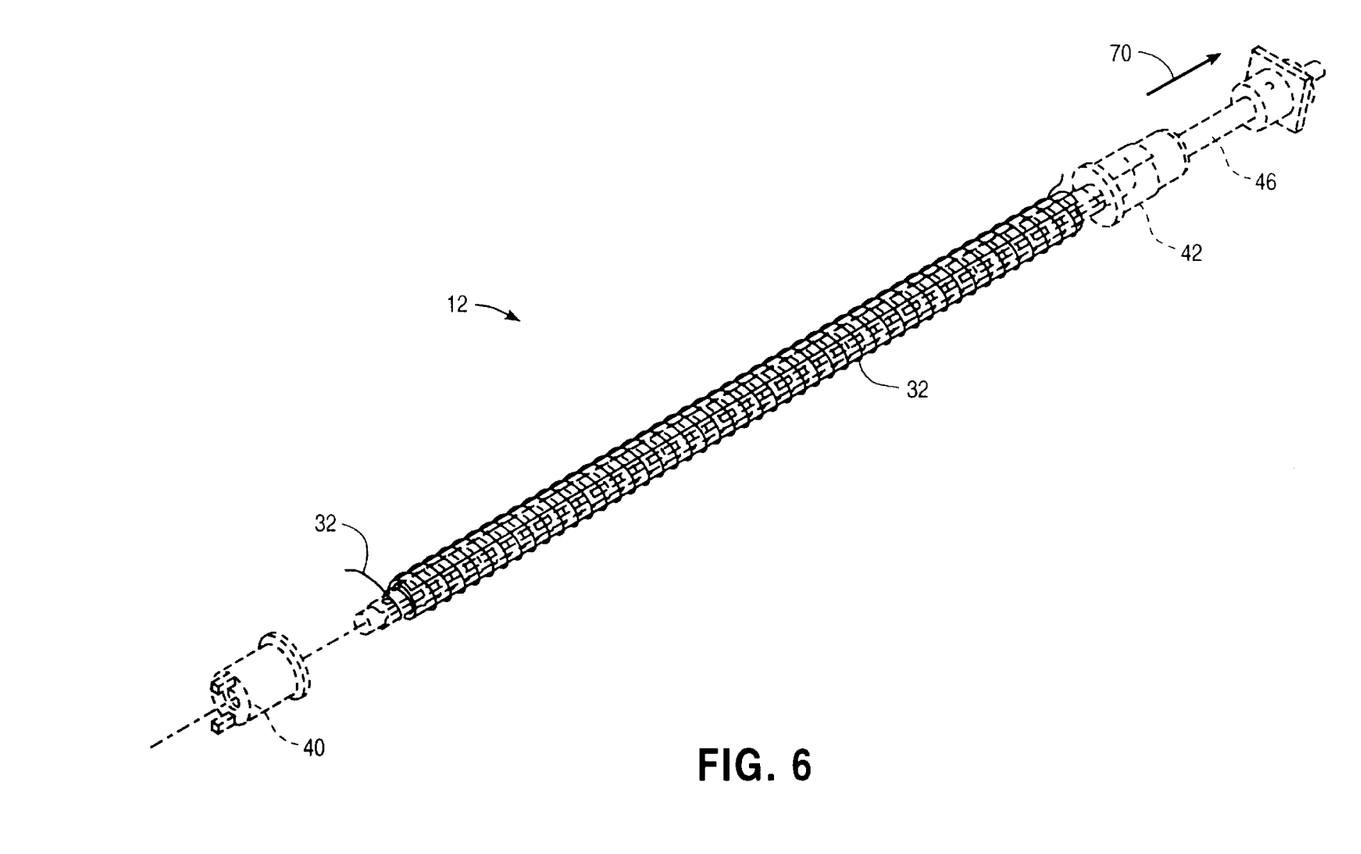
FIG. 6 illustrates disassembly of the prosthesis assembly mandrel of the tubular prosthesis assembly system of FIG. 1 after an outer helical frame component has been fully wrapped over a tissue sleeve thereon.
Figure 7:
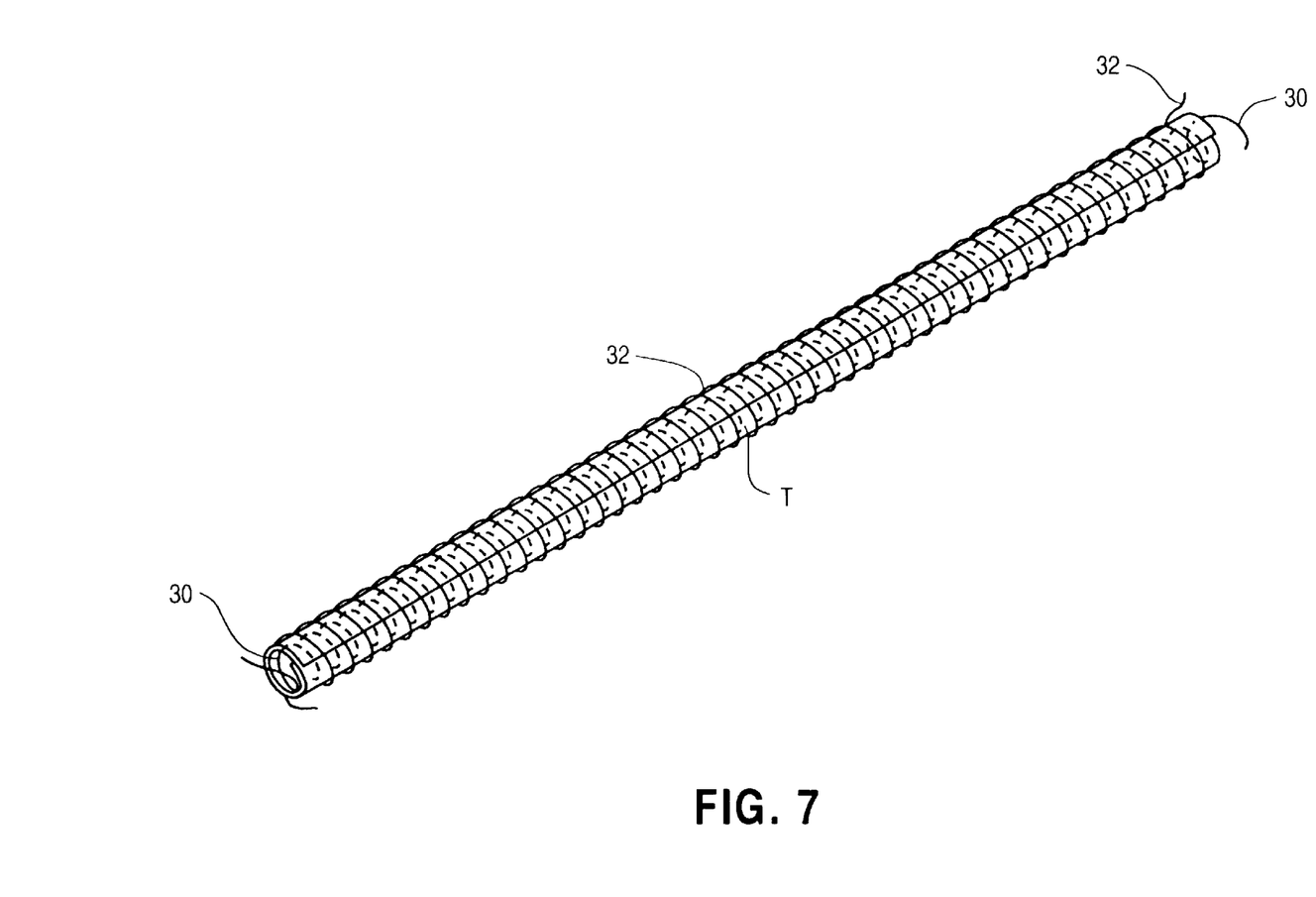
FIG. 7 illustrates the tubular prosthesis formed by the method and system of the present invention.

After the transfer of the outer helical frame component 32 to the prosthesis assembly mandrel 12 has been completed, it is necessary to remove the tubular prosthesis from the mandrel, as illustrated in FIG. 6. First, the mandrel 12 is lifted from the base structure 18. Next, the central core 46 is pulled axially, in the direction of arrow 70, from the mandrel 12, permitting the runners 48 to radially collapse and be withdrawn from inside the inner helical frame component 30. Both collets 40 and 42 are then pulled from the mandrel 12, leaving the free end of the outer helical frame component 32 loose, as shown. The tubular prosthesis is thus completed, as illustrated in FIG. 7. Typically, the ends of the tubular prosthesis will be trimmed and the free ends of the helical components 30 and 32 will be cut back from the tissue ends by a distance of from 1 mm to 4 mm. The end geometries will be prepared to facilitate forming anastomoses, typically by forming a straight, perpendicular edge or a beveled edge. Usually, the outer helical frame component 32 will be cut back first, followed by a circumcision of the tissue, with the inner helical frame component 30 being cut back last.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for forming a tubular prosthesis, said method comprising:

providing a sheet of tissue;

wrapping the sheet of tissue over a tubular inner frame member disposed over and in contact with a mandrel;

rotating the mandrel to draw a helical outer frame component over the wrapped tissue to form the tubular prosthesis; and collapsing and axially withdrawing the mandrel from the tubular inner frame member of the tubular prosthesis.

2. A method as in claim 1, wherein the sheet providing step comprises:

harvesting tissue from an animal host; and trimming the tissue into a shape selected to permit wrapping over the tubular inner frame.

3. A method as in claim 2, wherein the tissue is trimmed into a rectangular shape.

4. A method as in claim 1, wherein the tissue is selected from the group consisting of pericardium, fascia, rectus sheath, and venous tissue.

5. A method as in claim 1, further comprising treating the tissue with a cross-linking agent.

6. A method as in claim 5, wherein the tissue is treated by immersion in glutaraldehyde prior to attaching to the tubular inner frame member.

7. A method as in claim 1, further comprising implanting the prosthesis in a host.

8. A method as in claim 7, wherein the tissue was obtained from the same host into which the prosthesis is implanted.

9. A method as in claim 7, wherein the tissue was obtained from a host other than the host into which the prosthesis is implanted.

10. A method as in claim 1, wherein the tissue sheet is disposed over the inner frame member with parallel edges overlapping along a longitudinal line.

11. A method as in claim 10, wherein the edges are not connected other than by the outer helical frame component.

12. A method as in claim 11, wherein the edges overlap by an arc of at least 180°.

13. A method as in claim 1, wherein the wrapping step comprises placing an edge of the tissue over the tubular inner frame member and rotating the mandrel to wrap at least one and one-half turns of the tissue thereover.

14. A method as in claim 13, wherein from 1.5 to 3 turns of the tissue are wrapped thereover.

15. A method as in claim 1, wherein the tubular inner frame member comprises a helical inner frame component.

16. A method as in claim 1, further comprising guiding the helical outer frame component as it is being drawn onto the wrapped sheet of tissue.

17. A method as in claim 16, wherein the guiding step comprises rotating a lead screw, wherein the helical outer frame component is received in and advanced by a helical groove on said lead screw.

18. A method as in claim 1, wherein said collapsing step comprises withdrawing an inner support rod from an outer collapsible shell of the mandrel.

19. A method as in claim 18, wherein the collapsible shell comprises at least two axial runners which are aligned over a cylindrical support rod.

20. A method for forming a tubular prosthesis, said method comprising:

providing a sheet of tissue;

wrapping the sheet of tissue over a tubular inner frame;

axially aligning the wrapped tubular inner frame with a helical outer frame component;

coupling an end of the helical outer frame component to the wrapped tubular inner frame; and rotating the tissue-wrapped inner frame to draw the helical outer frame component over an outer surface of said tissue-wrapped inner frame, wherein the outer frame component forms an outer surface of the prosthesis.

21. A method as in claim 20, wherein the sheet providing step comprises:

harvesting tissue from an animal host; and trimming the tissue into a shape selected to permit wrapping over the tubular inner frame.

22. A method as in claim 21, wherein the tissue is trimmed into a rectangular shape.

23. A method as in claim 20, wherein the tissue is selected from the group consisting of pericardium, fascia, rectus sheath, and venous tissue.

24. A method as in claim 20, further comprising treating the tissue with a cross-linking agent.

25. A method as in claim 24, wherein the tissue is treated by immersion in glutaraldehyde prior to attaching to the tubular support frame.

26. A method as in claim 20, further comprising implanting the prosthesis in a host.

27. A method as in claim 26, wherein the tissue was obtained from the same host into which the prosthesis is implanted.

28. A method as in claim 26, wherein the tissue was obtained from a host other than the host into which the prosthesis is implanted.

29. A method as in claim 20, wherein the tissue sheet is disposed over the inner frame with parallel edges overlapping along a longitudinal line.

30. A method as in claim 29, wherein the edges overlap by an arc of at least 180°.

31. A method as in claim 20, further comprising guiding the helical outer frame component as the tissue-wrapped inner frame is rotated so that successive turns of said component are laid over said tissue-wrapped inner frame at a substantially equal pitch.

32. A method as in claim 31, wherein the guiding step comprises rotating a lead screw which is axially aligned with the tissue-wrapped inner frame and the helical outer frame component, wherein said component is received in and advanced by a helical groove on said lead screw.

33. A met hod as in claim 20, wherein the tubular inner frame is disposed over a mandrel, wherein the rotating step comprises rotating the mandrel.

34. A method as in claim 33, further comprising radially collapsing the mandrel and removing the collapsed mandrel from the tubular inner frame.

* * * * *